US009678635B2

(12) United States Patent
Wilkinson et al.

(10) Patent No.: US 9,678,635 B2
(45) Date of Patent: Jun. 13, 2017

(54) VISUAL PRESENTATION OF MULTI-DIMENSIONAL DATA SETS

(71) Applicant: QUEST DIAGNOSTICS INVESTMENTS INCORPORATED, Wilmington, DE (US)

(72) Inventors: Peter Wilkinson, Madison, NJ (US); Kerry O'Brien, Spring Hill, KS (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 226 days.

(21) Appl. No.: 13/731,761

(22) Filed: Dec. 31, 2012

(65) Prior Publication Data

US 2013/0339890 A1    Dec. 19, 2013

Related U.S. Application Data

(60) Provisional application No. 61/582,287, filed on Dec. 31, 2011.

(51) Int. Cl.
*G06F 3/0484* (2013.01)
*G06F 3/0482* (2013.01)
*G06F 19/00* (2011.01)

(52) U.S. Cl.
CPC .......... *G06F 3/0484* (2013.01); *G06F 3/0482* (2013.01); *G06F 19/3487* (2013.01)

(58) Field of Classification Search
CPC ............ G06F 3/0484; G06F 17/30678; G06F 17/30592
USPC .................. 715/771, 764; 345/440; 707/610; 702/83; 705/26.1; 434/107
See application file for complete search history.

(56) References Cited

U.S. PATENT DOCUMENTS

| | | | |
|---|---|---|---|
| 5,321,800 A * | 6/1994 | Lesser | 345/440 |
| 5,943,677 A * | 8/1999 | Hicks | 707/610 |
| 6,750,884 B1 * | 6/2004 | Steigerwald et al. | 715/771 |
| 7,165,065 B1 * | 1/2007 | Welton et al. | |
| 8,443,293 B2 * | 5/2013 | Soerensen et al. | 715/764 |
| 8,812,369 B2 * | 8/2014 | Jeong | 705/26.1 |
| 2002/0188424 A1 * | 12/2002 | Grinstein et al. | 702/183 |
| 2005/0267704 A1 * | 12/2005 | Huntley | 702/83 |
| 2007/0190499 A1 * | 8/2007 | Baur | 434/107 |
| 2011/0264561 A1 * | 10/2011 | Sundaresan | G06F 17/30678 705/27.1 |
| 2012/0089633 A1 * | 4/2012 | Vigneau | G06F 17/30592 707/769 |

* cited by examiner

*Primary Examiner* — Li Sun
*Assistant Examiner* — Jasmine Wan
(74) *Attorney, Agent, or Firm* — Joe E. Gordon; Haug Partners LLP

(57) ABSTRACT

Computer systems and methods may display multi-dimensional data sets in a dynamically-generated ocular view, which may show the relationship between data points in the different dimensions. For example, such a data set may include in one dimension results of one or more laboratory tests and, in another dimension, body systems or functions that the respective tests may relate to. The ocular view may depict the relationships between the tests and the systems. By being generated dynamically, moreover, the ocular view may be able to present this information for arbitrary sets of test results, without a template having been generated in advance to specify the layout of some particular combination of results.

21 Claims, 13 Drawing Sheets

VISUAL PRESENTATION OF MULTI-DIMENSIONAL DATA SETS

CROSS-REFERENCE TO RELATED APPLICATION

This application claims the benefit of U.S. provisional patent application 61/582,287, filed 31 Dec. 2012 and titled "Visual Presentation of Multi-Dimensional Data Sets", which is incorporated herein by reference.

COPYRIGHT NOTICE

A portion of the disclosure of this patent document contains material that is subject to copyright protection. The copyright owner has no objection to the facsimile reproduction by anyone of the patent document or the patent disclosure as it appears in the Patent and Trademark Office patent files or records but otherwise reserves all copyrights whatsoever.

BACKGROUND

Medical diagnosis and treatment have come to depend more and more on laboratory testing. As patients seek to become more involved in their own care, they have sought to better understand the results of their laboratory tests, yet existing forms of reports can often be confusing. There is thus a significant and growing need for improved ways to present laboratory test information (including test results) to patients.

BRIEF SUMMARY OF THE INVENTION

Embodiments of the invention relate to systems and methods for visually representing multi-dimensional data sets. Data points in multiple dimensions may be hierarchically related to one another, with the dimensions being ordered from highest to lowest. An ocular view of the data set may be prepared dynamically and presented on an electronic display device to a user, simplifying the presentation of data sets that may include complicated relationships between multiple data points in multiple dimensions.

The invention is illustrated particularly in connection with embodiments related to medical laboratory testing, but it is not limited to such embodiments.

According to an embodiment of the invention, a method of causing a display on an electronic display device of a representation of a multi-dimensional data set, is performed by a computer system that comprises one or more processors and one or more interfaces operatively coupled to at least one of the processors. The method comprises receiving through at least one of the interfaces data representing the multi-dimensional data set, where: (1) the data set comprises a plurality of data points in a plurality of dimensions; (2) the dimensions are ordered from lowest to highest; (3) each data point in each dimension other than the lowest is associated respectively with exactly one of the data points in the immediately lower dimension, and each data point in each dimension other than the highest being associated respectively with one or more of the data points in the immediately higher dimension; and (4) each data point comprises at least one value.

According to the method, at least one of the processors, in response to receiving the data, executes instructions to dynamically calculate layout data for an ocular view of the data set. The method also comprises transmitting through at least one of the interfaces information based on the layout data to cause the electronic display device to present at a single time the ocular view of the data, where: (1) the ocular view comprises a plurality of concentric annular regions surrounding a circular region; (2) the annular regions are in one-to-one correspondence with the dimensions of the data set; (3) each annular region is divided into contiguous segments and subtends respectively an angle that has its vertex at the center of the annular region; (4) the segments in each annular region are in one-to-one correspondence with the data points in the corresponding dimension of the data set; (5) all the segments are mutually aligned so that the first angle subtended by a first segment overlaps with the second angle subtended by a second segment that is in an annular region immediately adjacent to the annular region containing the first segment if and only if the data point corresponding to the first segment is associated with the data point corresponding to the second segment; and (6) each segment displays at least one of the values in the respective corresponding data point.

In an embodiment of the invention, at least one of the processors executes instructions to determine that a user interface pointer is pointing at one of the segments in the annular region that corresponds to the highest dimension. The method also comprises, in response to determining that the pointer is pointing at the segment, transmitting through at least one of the interfaces information that causes the electronic display to modify the appearance of the segment being pointed to, while continuing to present the ocular view. The method also comprises, in response to determining that the pointer is pointing at the segment, transmitting through at least one of the interfaces information causing the electronic display to present in the circular region at least one of the values comprised by the data point corresponding to the segment being pointed to.

In an embodiment of the invention, the method comprises transmitting through at least one of the interfaces information to cause the electronic display device to present a separate information region contemporaneously with the ocular view. The method also comprises, in response to determining that the pointer is pointing at the segment, transmitting through at least one of the interfaces information causing the electronic display to present in the information region information that is associated with at least one of the values comprised by a data point that is associated with the data point corresponding to the segment being pointed to.

In an embodiment of the invention, the data set represents a plurality of results from a panel of laboratory tests. In one such embodiment, each data point in the highest dimension of the data set represents exactly one result of exactly one laboratory test, each data point in the second-highest dimension of the data represents an organ or body system, and the relative alignments of segments in the outermost annular region and the second-outermost annular region reflect one or more relationships between the test results and organs or body systems that respectively correspond to the segments.

Embodiments of the invention also include computer systems configured to carry out the above methods. Further embodiments of the invention include computer-readable storage media encoded with instructions that, when executed by at least one processor within a suitably-configured computer system, cause the computer system to carry out the above methods.

DETAILED DESCRIPTION OF PREFERRED EMBODIMENTS

Figure 1:
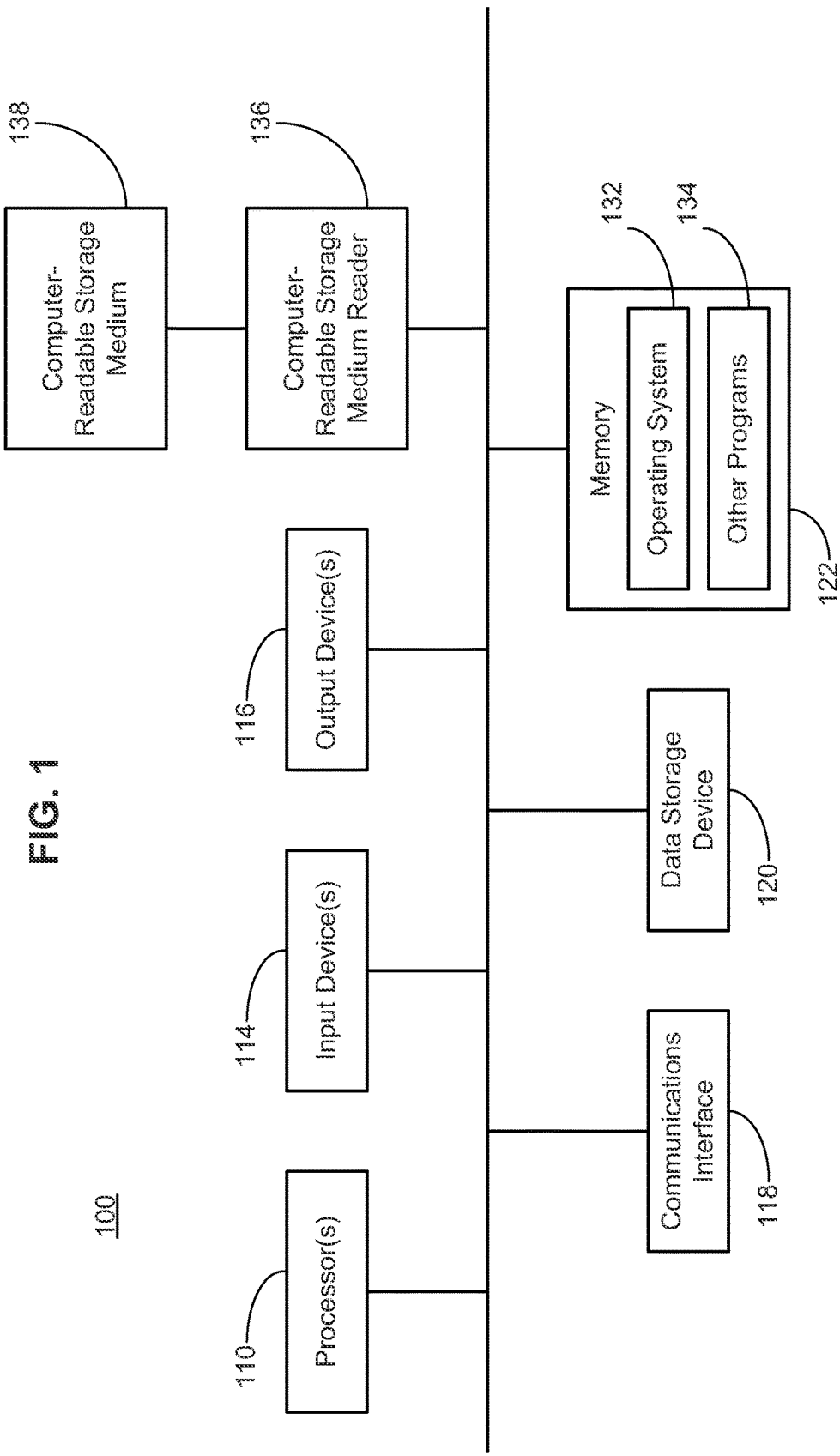
FIG. 1 is a block diagram depicting an exemplary computer system with which embodiments of the invention may at least partially be implemented.

Embodiments of the invention may be implemented by systems using one or more programmable digital computers. FIG. 1 depicts an example of one such computer system 100, which includes at least one processor 110, such as, e.g., an Intel or Advanced Micro Devices microprocessor, coupled to a communications channel or bus 112. The computer system 100 further includes at least one input device 114 such as, e.g., a keyboard, mouse, touch pad or screen, or other selection or pointing device, at least one output device 116 such as, e.g., an electronic display device, at least one communications interface 118, at least one data storage device 120 such as a magnetic disk or an optical disk, and memory 122 such as ROM and RAM, each coupled to the communications channel 112. The communications interface 118 may be coupled to a network (not depicted) such as the Internet.

Although the computer system 100 is shown in FIG. 1 to have only a single communications channel 112, a person skilled in the relevant arts will recognize that a computer system may have multiple channels (not depicted), including for example one or more busses, and that such channels may be interconnected, e.g., by one or more bridges. In such a configuration, components depicted in FIG. 1 as connected by a single channel 112 may interoperate, and may thereby be considered to be coupled to one another, despite being directly connected to different communications channels.

One skilled in the art will recognize that, although the data storage device 120 and memory 122 are depicted as different units, the data storage device 120 and memory 122 can be parts of the same unit or units, and that the functions of one can be shared in whole or in part by the other, e.g., as RAM disks, virtual memory, etc. It will also be appreciated that any particular computer may have multiple components of a given type, e.g., processors 110, input devices 114, communications interfaces 118, etc.

The data storage device 120 (FIG. 1) and/or memory 122 may store instructions executable by one or more processors or kinds of processors 110, data, or both. Some groups of instructions, possibly grouped with data, may make up one or more programs, which may include an operating system 132 such as, e.g., Microsoft Windows® 7, Linux®, Mac OS®, or Unix®. Other programs 134 may be stored instead of or in addition to the operating system. It will be appreciated that a computer system may also be implemented on platforms and operating systems other than those mentioned. Any operating system 132 or other program 134, or any part of either, may be written using one or more programming languages such as, e.g., Java®, C, C++, C#, Visual Basic®, VB.NET®, Perl, Ruby, Python, or other programming languages, possibly using object oriented design and/or coding techniques.

One skilled in the art will recognize that the computer system 100 (FIG. 1) may also include additional components and/or systems, such as network connections, additional memory, additional processors, network interfaces, input/output busses, for example. One skilled in the art will also recognize that the programs and data may be received by and stored in the system in alternative ways. For example, a computer-readable storage medium (CRSM) reader 136, such as, e.g., a magnetic disk drive, magneto-optical drive, optical disk drive, or flash drive, may be coupled to the communications channel 112 for reading from a CRSM 138 such as, e.g., a magnetic disk, a magneto-optical disk, an optical disk, or flash memory. Alternatively, one or more CRSM readers may be coupled to the rest of the computer system 100, e.g., through a network interface (not depicted) or a communications interface 118. In any such configuration, however, the computer system 100 may receive programs and/or data via the CRSM reader 136. Further, it will be appreciated that the term "memory" herein is intended to include various types of suitable data storage media, whether permanent or temporary, including among other things the data storage device 120, the memory 122, and the CSRM 138.

(Unless explicitly stated otherwise, the term "computer-readable storage medium" herein specifically excludes transitory propagating signals, as should already be clear from the word "storage".)

Figure 2:
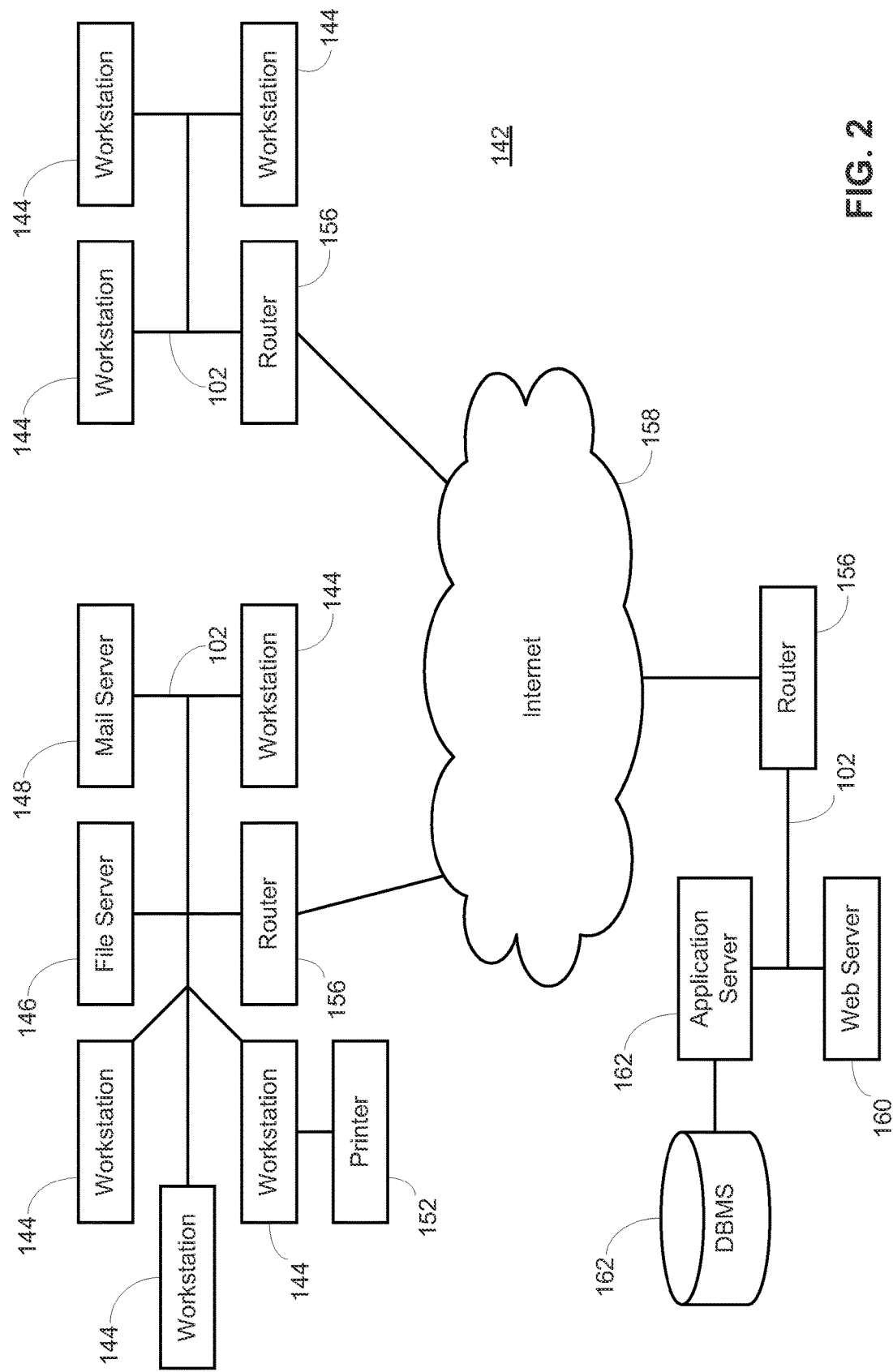
FIG. 2 is a block diagram depicting an exemplary interconnected network with which embodiments of the invention may at least partially be implemented.

Two or more computer systems 100 (FIG. 1) may communicate, e.g., in one or more networks, via, e.g., their respective communications interfaces 118 and/or network interfaces (not depicted). FIG. 2 is a block diagram depicting an example of one such interconnected network 142. Network 142 may, for example, connect one or more workstations 144 with each other and with other computer systems, such as file servers 146 or mail servers 148. A workstation 144 may comprise a computer system 100. The connection may be achieved tangibly, e.g., via Ethernet® or optical cables, or wirelessly, e.g., through use of modulated microwave signals according to the IEEE 802.11 family of standards. A computer workstation 144 or system 100 that participates in the network may send data to another computer workstation system in the network via the network connection.

One use of a network 142 (FIG. 2) is to enable a computer system to provide services to other computer systems, consume services provided by other computer systems, or both. For example, a file server 146 may provide common storage of files for one or more of the workstations 144 on a network 142. A workstation 144 sends data including a request for a file to the file server 146 via the network 142 and the file server 146 may respond by sending the data from the file back to the requesting workstation 144.

Further, a computer system may simultaneously act as a workstation, a server, and/or a client. For example, as depicted in FIG. 2, a workstation 144 is connected to a printer 152. That workstation 144 may allow users of other workstations on the network 142 to use the printer 152, thereby acting as a print server. At the same time, however, a user may be working at the workstation 144 on a document that is stored on the file server 146.

The network 142 (FIG. 2) may be connected to one or more other networks, e.g., via a router 156. A router 156 may also act as a firewall, monitoring and/or restricting the flow of data to and/or from the network 142 as configured to protect the network. A firewall may alternatively be a separate device (not pictured) from the router 156.

An internet may comprise a network of networks 142 (FIG. 2). The term "Internet" refers to the worldwide network of interconnected, packet-switched data networks that uses the Internet Protocol (IP) to route and transfer data. For example, a client and server on different networks may communicate via the Internet 158, e.g., a workstation 144 may request a World Wide Web document from a Web server 160. The Web server 160 may process the request and pass it to, e.g., an application server 162. The application server 162 may then conduct further processing, which may include, for example, sending data to and/or receiving data from one or more other data sources. Such a data source may include, e.g., other servers on the same computer system 100 or LAN 102, or a different computer system or LAN and/or a database management system ("DBMS") 162.

As will be recognized by those skilled in the relevant art, the terms "workstation," "client," and "server" are used herein to describe a computer's function in a particular context. A workstation may, for example, be a computer that one or more users work with directly, e.g., through a keyboard and monitor directly coupled to the computer system. A computer system that requests a service through a network is often referred to as a client, and a computer system that provides a service is often referred to as a server. But any particular workstation may be indistinguishable in its hardware, configuration, operating system, and/or other software from a client, server, or both.

The terms "client" and "server" may describe programs and running processes instead of or in addition to their application to computer systems described above. Generally, a software client may consume information and/or computational services provided by a software server.

Figure 3:
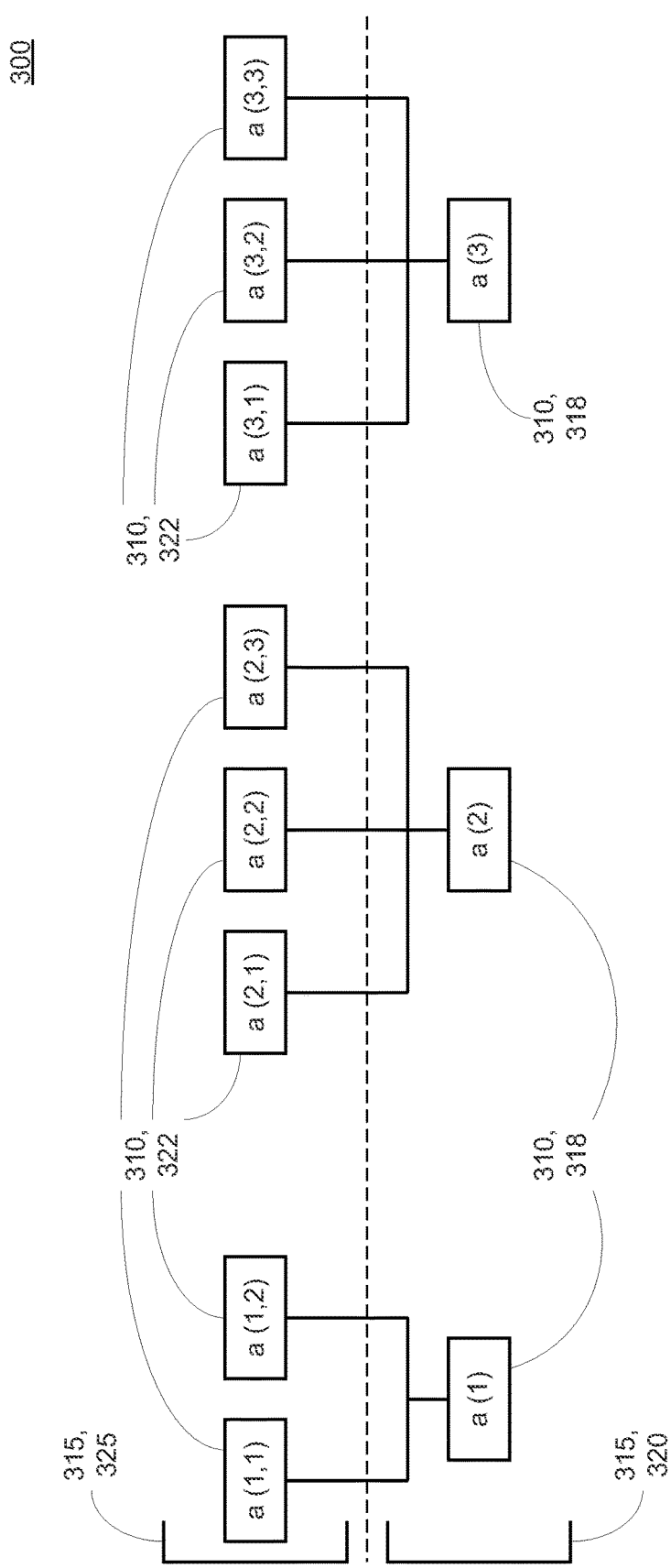
FIG. 3 illustrates a simple multi-dimensional data set such as may be presented by an embodiment of the invention.

FIG. 3 depicts the organization of a sample multi-dimensional data set 300 in connection with an embodiment of the invention. The depicted data set 300 consists of a plurality of data points 310 in two dimensions 315. The data points 310 are associated with each other hierarchically: each data point 318 in the first or lowest dimension 320 is associated with one or more data points 322 in the second or (in the depicted example) highest dimension 325, but each data point 322 in the second dimension 325 is associated with exactly one data point 318 in the first dimension 320.

Figure 4:
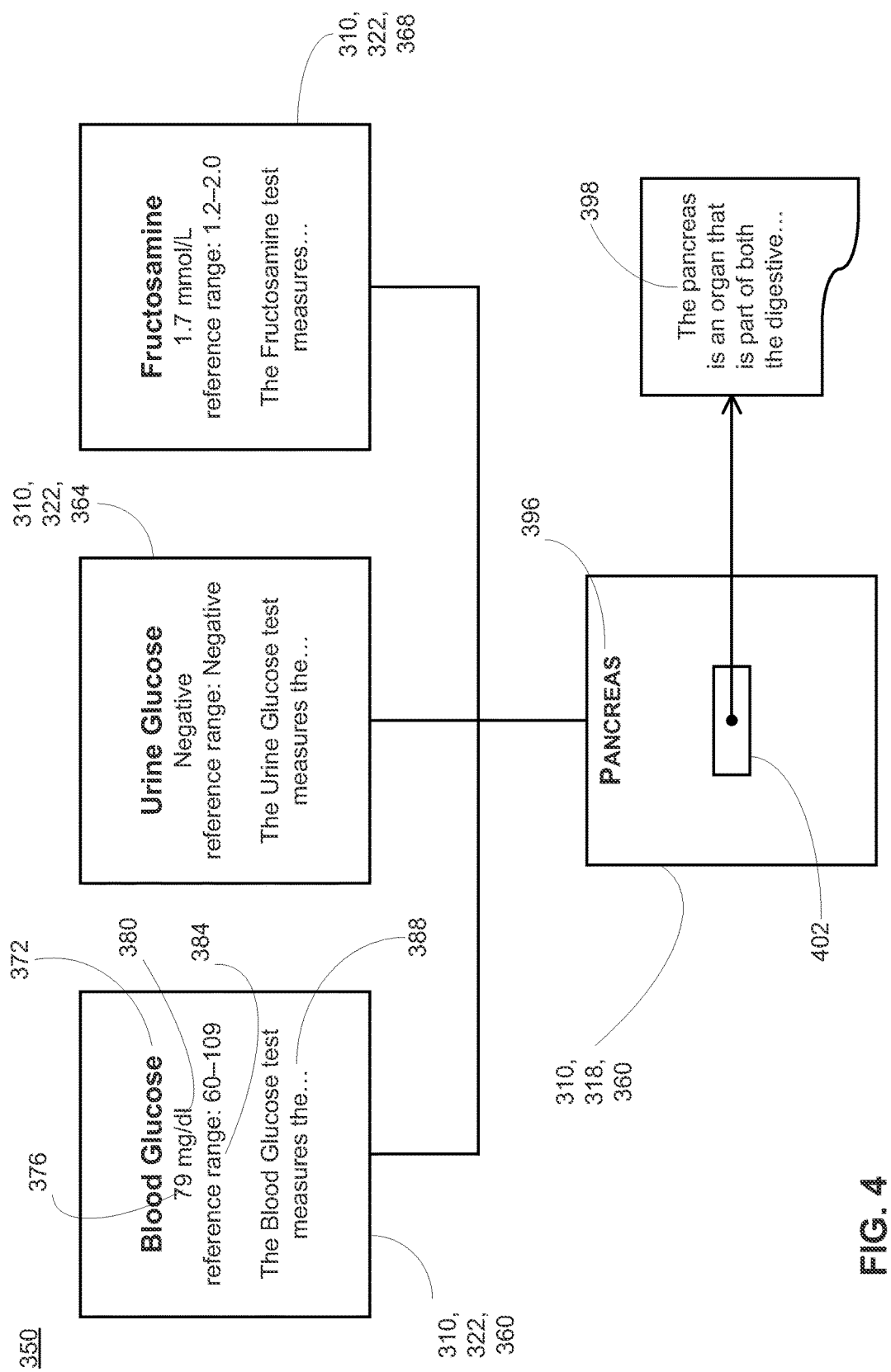
FIG. 4 depicts details of some data points in a data set such as FIG. 3 depicts.

FIG. 4 depicts the contents of several related data points 310 in more detail, illustrating the relationship between those contents and the associations between the data points in connection with an embodiment of the invention. The data points in the lowest dimension 322 correspond to individual analytes measured in one or more panels of laboratory tests performed on a patient. As depicted, one data point 360 corresponds to a measurement of blood glucose, another 364 corresponds to a measurement of urine glucose, and a third 368 corresponds to a measurement of fructosamine.

As depicted, the data points 322 each include one or more values related to the analyte, the measurement, or both. For example, the data point 360 corresponding to a blood glucose test includes a test identifier 372, a numerical measurement 376 of that analyte and the units 380 of that measurement, the reference range 384 for that test, and an explanation 388, e.g., of the analyte and its significance.

These analytes may be related to pancreatic function in the patient. The corresponding data points 322 are therefore associated with a data point 392 in the second dimension that corresponds the pancreas. As depicted, such a data point may include an identifier 396 for the organ and/or body system and an explanation 398 of the function or role of the organ and/or system in the body.

The depictions in FIGS. 3 and 4 are meant to illustrate logical relationships only and will not necessarily correspond to any representation of any data set in connection with an embodiment of the invention. Many representations of a multidimensional data set, such as may be suitable for use in connection with an embodiment of the invention, will be apparent to those skilled in the relevant arts. For example, in an embodiment of the invention, each dimension of a data set may correspond to a table or view in a relational database (not pictured), where each row corresponds to a data point, and associations between data points may be represented, e.g., by foreign key constraints.

A data set 300 in connection with an embodiment may have relationships and/or associations in addition to those depicted in FIGS. 3 and 4. But if displayed in an ocular view, e.g., as described and depicted herein, the data points may be considered to have only those relationships and/or associations such as are implicit in the ocular view.

In an embodiment of the invention, a representation of a data point may include one or more values directly, e.g., as a field in a data structure and/or row in a data table. In addition to or instead of directly including values, however, a field may include some or all values indirectly. For example, as FIG. 4 depicts, the data point 392 corresponding to the pancreas directly includes the identifier "Pancreas" 396, but includes the description 398 indirectly, including directly only a pointer 402 to the description 398. The data point 392 may nonetheless be considered to include both the identifier 396 and the description 398.

Figure 5:
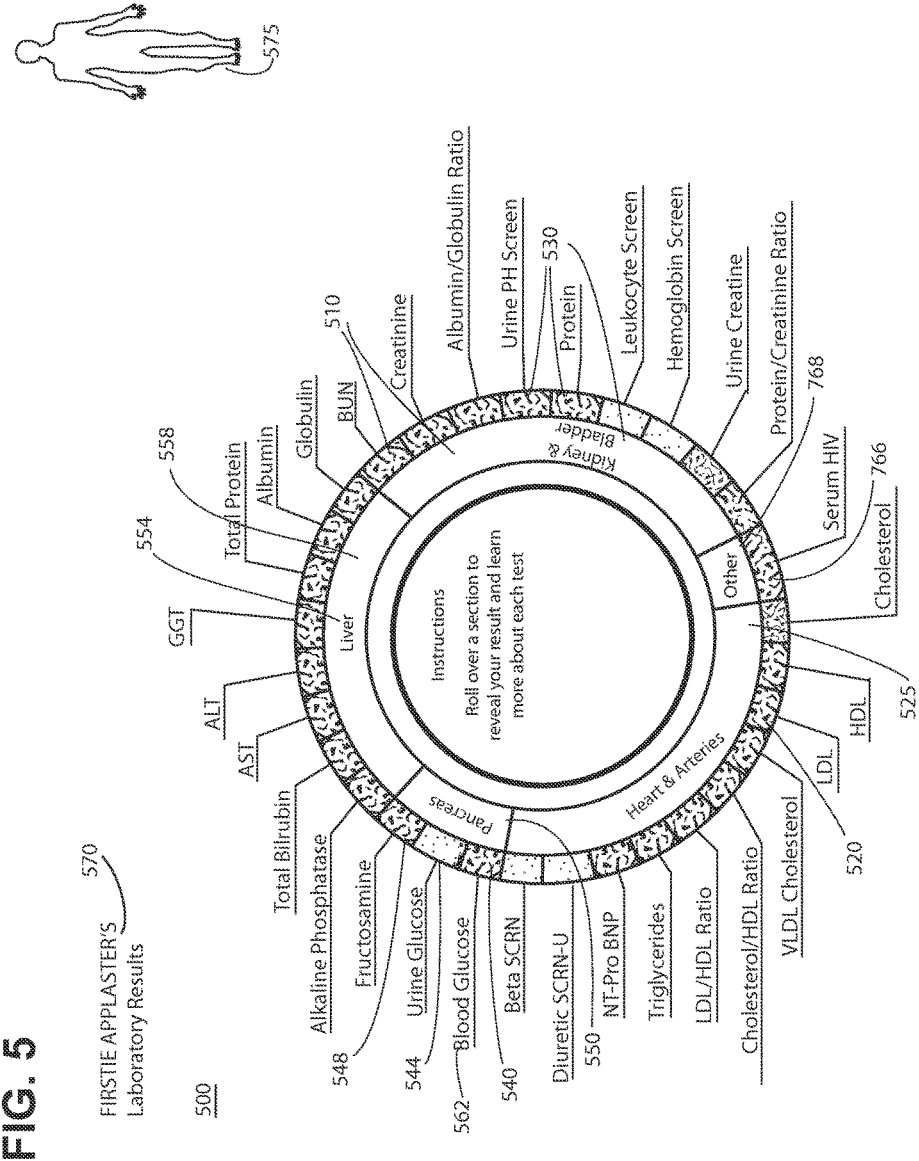
FIG. 5 depicts an exemplary ocular view of a multi-dimensional data set according to an embodiment of the invention.

FIG. 5 depicts an exemplary ocular view 500 of a multidimensional data set, e.g., such as FIGS. 3 and 4 may partially depict, which a computer system may present according to an embodiment of the invention. An ocular view according to an embodiment of the invention may comprises a plurality of concentric annular regions, where each region corresponds respectively to one dimension of the data set. For example, as depicted, the ocular view 500 comprises two concentric annular regions 510 (which may be called "rings" herein), each corresponding respectively to one dimension 315 (FIG. 3) of a data set 300 (FIG. 3). In an embodiment of the invention, the outermost ring 520 corresponds to the highest dimension 325 (FIG. 3) of the data set, while the innermost ring 525 corresponds to the lowest dimension 320 (FIG. 3) of the data set.

In an embodiment of the invention, each ring 510 is divided into segments 530. Each segment 530 corresponds to a single data point of the data set. For example, as depicted, the segments numbered 540, 544, and 548 of the outer ring correspond respectively to the data points numbered 360, 364, and 368 in FIG. 4, and the segment numbered 550 in FIG. 5 corresponds to the data point numbered 392 in FIG. 4.

As depicted, narrow spacers appear between the segments 530 in each ring. Such spacers may be included in an ocular view 500 according to an embodiment of the invention, e.g., to improve visibility. The spacers may in an embodiment of the invention be considered part of either segment they separate, neither segment, and/or part of one segment on one side and part of the other segment on the other side. In an embodiment of the invention, some or all of the spacers may be treated differently for different purposes (e.g., calculation of layout vs. selection of segments).

As depicted, some or all segments may be labeled to indicate what they stand for. For example, a label 554 inside a segment 558 may indicate the organ or body system (e.g., the liver) that the segment 558 is associated with. Alternatively, a label 562 may be placed outside of a segment 562 but visually associated with it in a way that illustrates the connection.

In an embodiment of the invention, the relationships between the data points in the respective dimensions may be indicated by the relative placement of the segments that correspond to the data points. For example, as FIG. 5 depicts, the segment 550 that corresponds to the pancreas subtends an angle with its vertex at the shared center of the concentric rings. The higher-dimensioned segments 540, 544, and 548 that correspond to the analytes that are associated with the pancreas each subtend respective angles within that angle subtended by the pancreas segment 550. (An angle may be considered to be "within" another angle for this purpose even though the angles have one or both sides in common.)

As depicted in FIG. 5, an ocular view 500 according to an embodiment of the invention may sometimes omit the precise measurements of some or all measured values for the analytes. It will be observed, for example, that no numerical measurement is displayed in FIG. 5.

Nonetheless, an ocular view 500 may provide some information about values non-numerically. In an embodiment of the invention, the color of the segment 530 may indicate whether the measured value falls within a predefined "reference range" or some predefined range of measurements that may be considered normal. For example, in one such embodiment, if a measured value falls within the reference range, the corresponding segment may be green, but if the value does not, the corresponding segment may be yellow or orange.

As is known in the art, some laboratory tests do not typically give numeric values, but are reported "positive" or "negative". For such tests, in an embodiment of the invention, the segment corresponding to the test or analyte may be colored green if the result is negative and orange if the result is positive. Alternatively, the nature of the test may be indicated by coloring the corresponding segment differently for either or both results (e.g., the segment may be colored tan or olive green if the test is negative but orange if the test is positive). It will be appreciated that an ocular view 500 according to an embodiment of the invention may thereby report the precise result of a positive/negative test without verbally or numerically providing that result.

An ocular view 500 according to an embodiment of the invention may be accompanied by other information. For example, as FIG. 5 depicts, the ocular view 500 is accompanied by a label that indicates what data the ocular view represents. The depicted ocular view 500 is also accompanied by an information region 575, which may present additional information, e.g., as described below.

In an embodiment of the invention, the ocular view 500 may interact with the user to present information more clearly and cleanly. It will be observed that, as FIG. 5 depicts, no numeric value is presented explicitly for any analyte.

Figure 6:
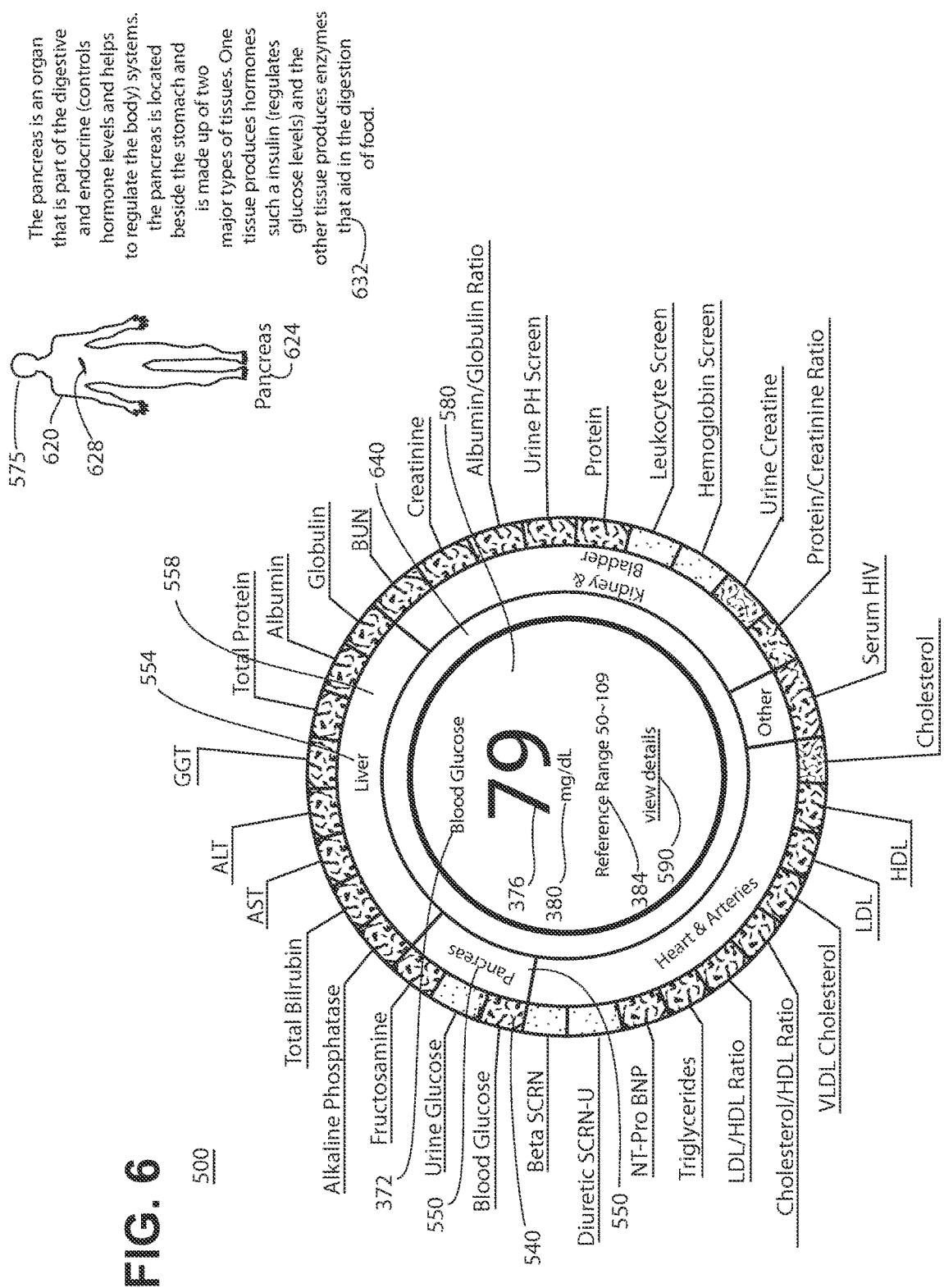
FIG. 6 depicts an exemplary ocular view with a selected data point.

FIG. 6 depicts an ocular view 500 after a user has selected a segment that corresponds to a data point that represent a particular measurement of a particular analyte, according to an embodiment of the invention. (For brevity, the user may be said herein to select the analyte in this case.) As depicted, the user has selected the segment 540 that corresponds to the measurement of blood glucose. In response to the user's selection, some or all values from that data point 360 (FIG. 4) may be added to the ocular view 500. For example, as depicted, a circular central region 580 (which may be referred to as the "detail area"), inside the innermost ring 525, displays the values from the data point 360, including the identifier 372, numerical measurement 376, units 380, and reference range 384.

Figure 7:
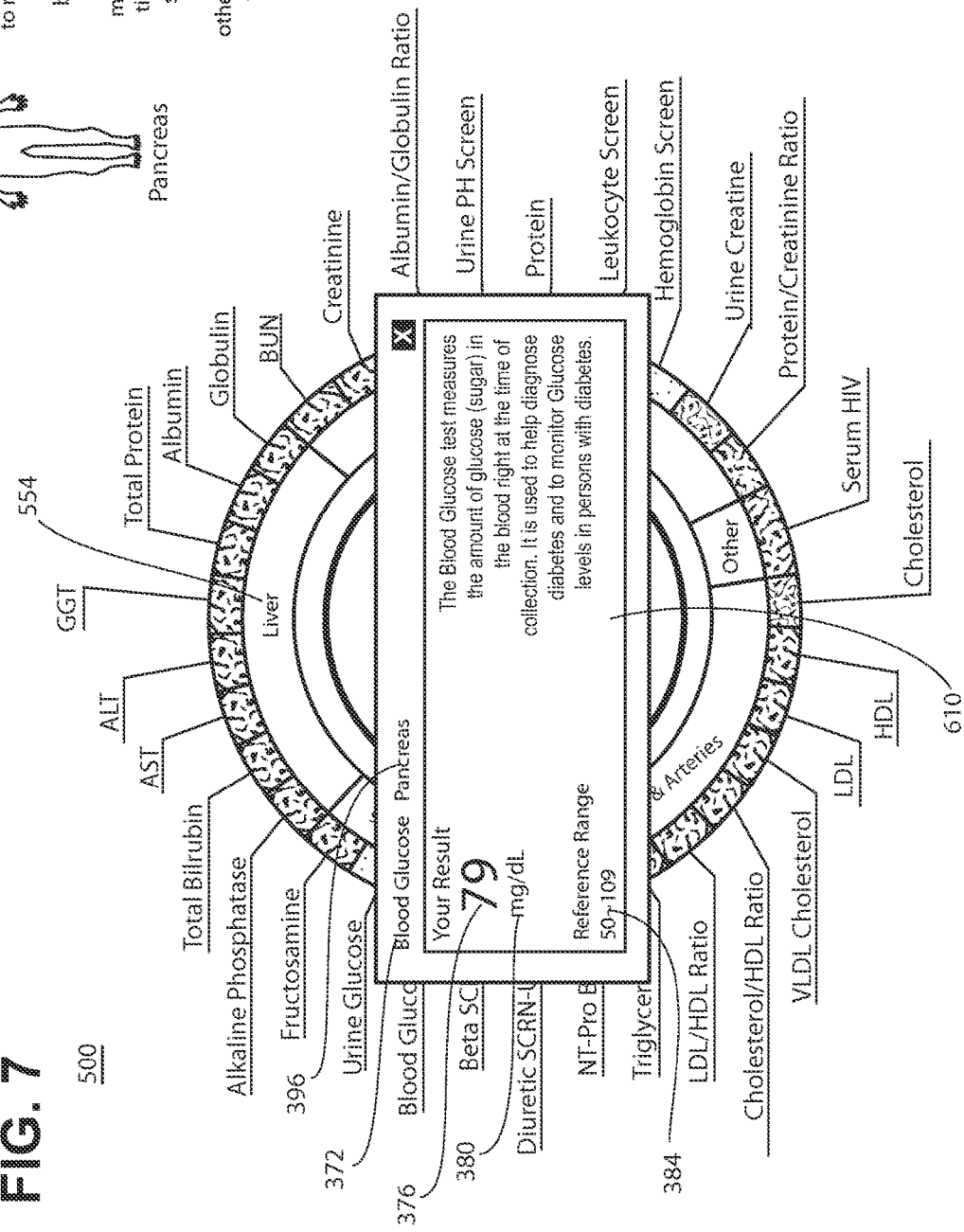
FIG. 7 depicts presentation of additional information related to a selected data point.

In an embodiment such as FIG. 6 depicts, the detail area 580 may also include a hyperlink 590 or other control that a user may select to obtain more data about the measurement. For example, the detail area 580 in FIG. 6 includes the text "view details", which, when selected may cause, e.g., a pop-up window to appear, possibly such as the window 600 that FIG. 7 depicts. In an embodiment of the invention, the pop-up window 600 may include some or all of the values displayed in the detail area 580 of FIG. 6. The pop-up window 600 may also include, however, a description 610, e.g., of the blood glucose test, what it measures, and/or its relevance to the patient's health. The depicted pop-up 600 also includes the identifier 396 of the organ or body system to which the analyte is related, from the associated data point 392 (FIG. 4) in the immediately lower dimension 320 (FIG. 4).

Returning to FIG. 6, selection of an analyte may cause related information to be displayed in the information region 575. For example, in an embodiment such as FIG. 6 depicts, selection of an analyte may cause display of information about the organ or body system associated with the analyte.

When blood glucose is selected, in an embodiment of the invention, that organ is the pancreas, and in response, the information region 575 is made to display information about the pancreas. For example, in an embodiment of the invention, the information region 575 may include a silhouette 620 or other representation of a human body and/or a label 624. As depicted, when an analyte associate with the pancreas is selected, the label 624 may be set to "Pancreas", and the representation 620 may have an region highlighted 628 or otherwise be modified to illustrate, e.g., the location, size, and/or shape of the pancreas. Elsewhere, e.g., in the information region 575 or adjacent to it (which may depend as much on how the "information region" is defined as much as anything else), further information 632 about the pancreas or other relevant organ or body system may also be displayed.

Selection of an analyte may in an embodiment of the invention may be indicated elsewhere in the ocular view 500 in one or more ways in addition to some or all of the foregoing. For example, the selected segment 540 may change in color (e.g., by lightening or darkening) or otherwise be highlighted, and/or the appearance of the selected segment may otherwise change to reflect selection.

The ocular view 500 may further change to reflect the organ or body system that is associated with the selected analyte. For example, one element of the ocular view 500 in an embodiment such as FIG. 6 depicts is a neutral colored ring 640 inside the ring 525 that corresponds to the lowest dimension of the data set. In the depicted embodiment, when an analyte is selected, the segment in the adjacent ring 525 that corresponds to the associated organ or body system changes color to match the neutral colored ring 640. As a more concrete example, when the analyte blood glucose 540 is selected, the segment 550 of the inner ring 525 that corresponds to the pancreas changes color, and the inner border of the segment disappears, so that the segment 550 appears in some sense to be a projection from the neutral ring 640 into the inner ring 525.

Figure 8:
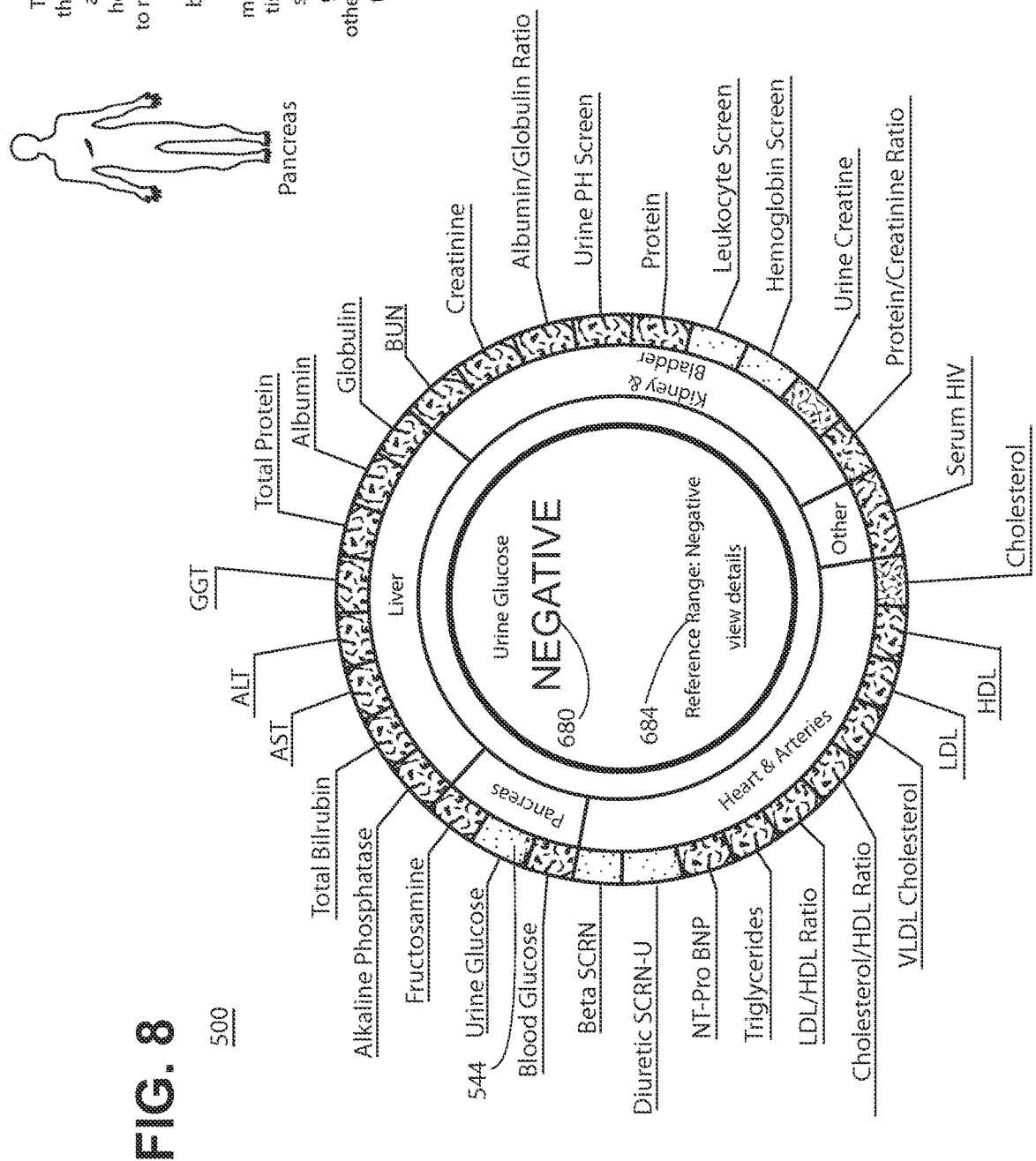
FIGS. 8 and 9 depict exemplary ocular views with selected data points.

FIG. 8 depicts the slightly varied appearance of the ocular view 500, according to an embodiment of the invention, when the selected analyte is not given a numerical measurement, but is reported, e.g., as either positive or negative. As depicted, the user has selected urine glucose 544 as the analyte. The detail area 580 displays the result 680, which may be positive or (as displayed) negative, and indicates that the reference range 684 for this analyte is negative.

Figure 9:
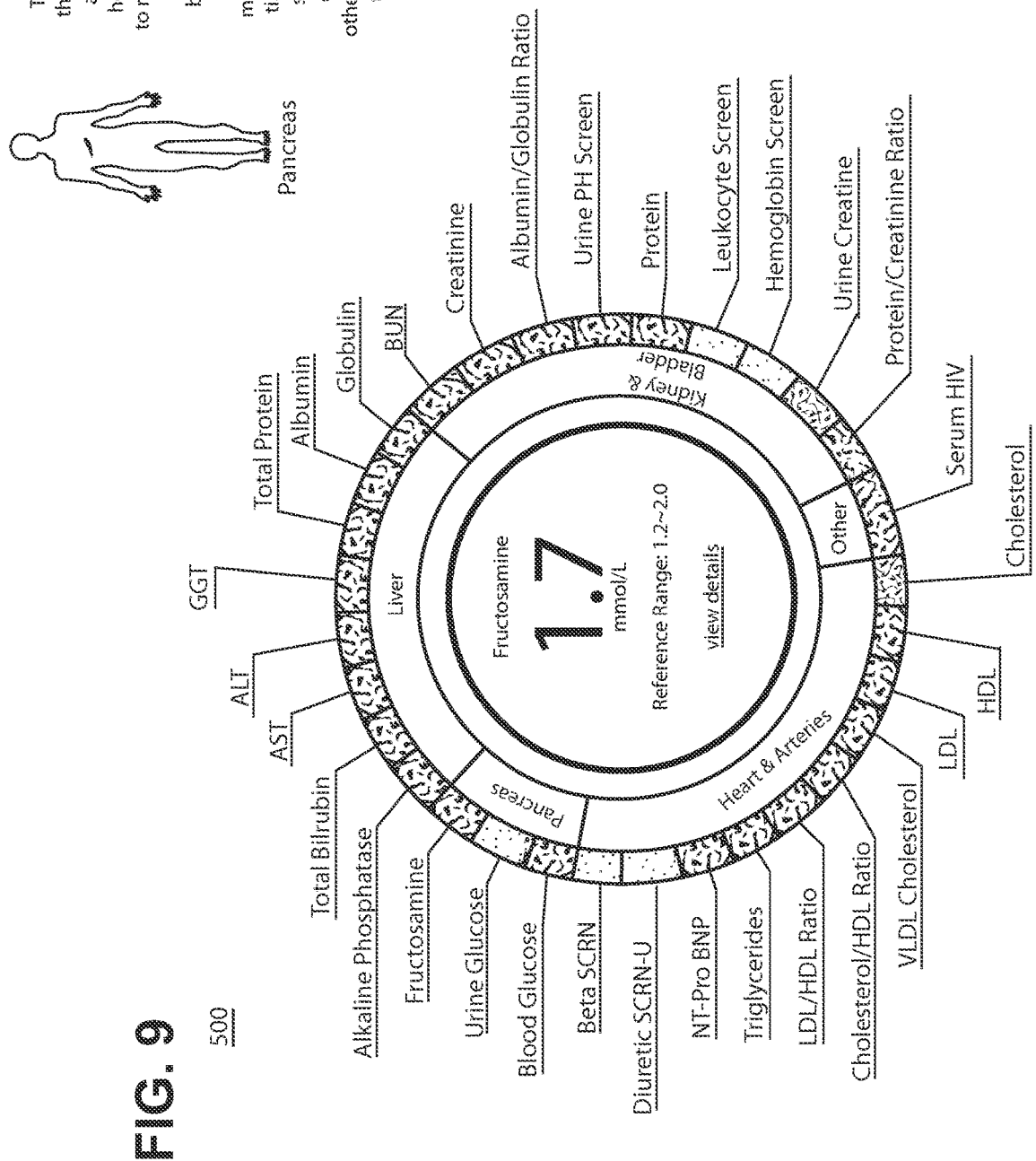

FIG. 9 depicts the ocular view 500 when fructosamine is the selected analyte.

In discussing the ocular view 500 in connections with FIGS. 6-9, repeated reference has been made to selection of a segment 510 of the outermost ring 520. As used in the art, "selection" may commonly mean, in connection with a graphical user interface, that a user uses a pointing device (e.g., a mouse, joystick, track pad, or trackball) to move a pointer on the screen to an object to be selected and then, while the pointer points to the object, selects the object by clicking (i.e., pressing and then releasing) a button on the pointing device. In describing embodiments of the invention herein, selection of a segment may refer to such a procedure, but it need not be limited to it.

For example, in an embodiment of the invention, a user may select a segment merely by using the pointing device to move the on-screen pointer to the segment. In such an embodiment, the user may not need to click to select the segment; a "mouse-over" gesture may suffice. In one such embodiment, a segment may remain selected, even though the user moves the pointer to another part of the display, until the user selects a different segment. Embodiments of the invention may support selection according to one or more procedures and/or user interface conventions in addition to or instead of either or both of the selection procedures described herein.

Figure 10:
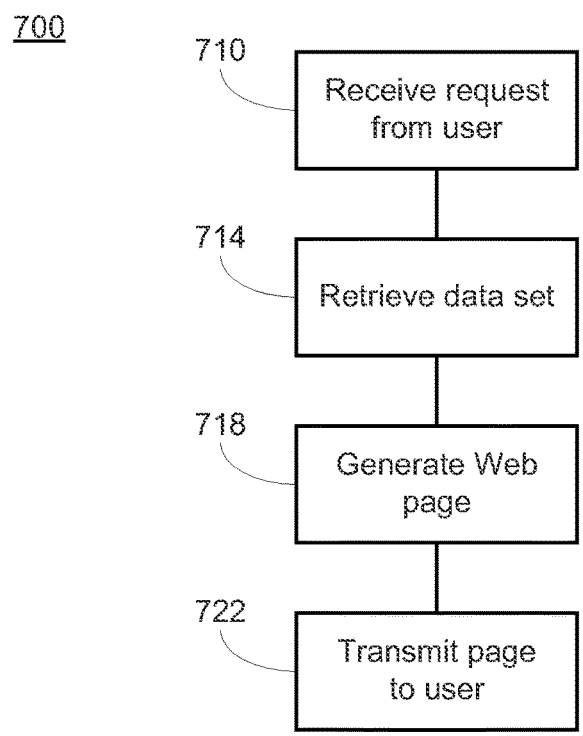
FIG. 10 depicts the flow of creating an ocular view according to an embodiment of the invention.

FIG. 10 depicts the flow 700 of creating an ocular view of a data set according to an embodiment of the invention. The flow begins in block 710, where a request for the data set is received. In a Web-based implementation, this request may take the form of one or more HTTP queries generated from a browser or other user agent, which may be transmitted through one or more computer networks to a server configured to respond to the request.

In response to the request, in block 714, a server may request a multi-dimensional data set from, e.g., a database management system (DBMS).

On receiving the data set, the server may in block 718 generate a Web page responsive to the request. As is known in the art, a Web page may be defined by text marked up according to a language such as HTML, XHTML, or XML, typically combined with one or more style sheets and JavaScript code, which may be included in one or more of the marked-up text files, one or more separate JavaScript files, or both. Style sheets may describe the desired appearance of one or more classes of elements in the page, and the form, content, and/or appearance of the page may be modified by JavaScript programs.

In an embodiment of the invention, a representation of the data set may be created on the page in the form of one or more JavaScript function calls, assignments, and/or other statement. The visual layout of the ocular view may be computed, e.g., by a server, which may encode the layout using JavaScript, or by the client, such as a browser, which may execute one or more statements and/or functions to calculate the layout based on the encoded data set.

Figure 11:
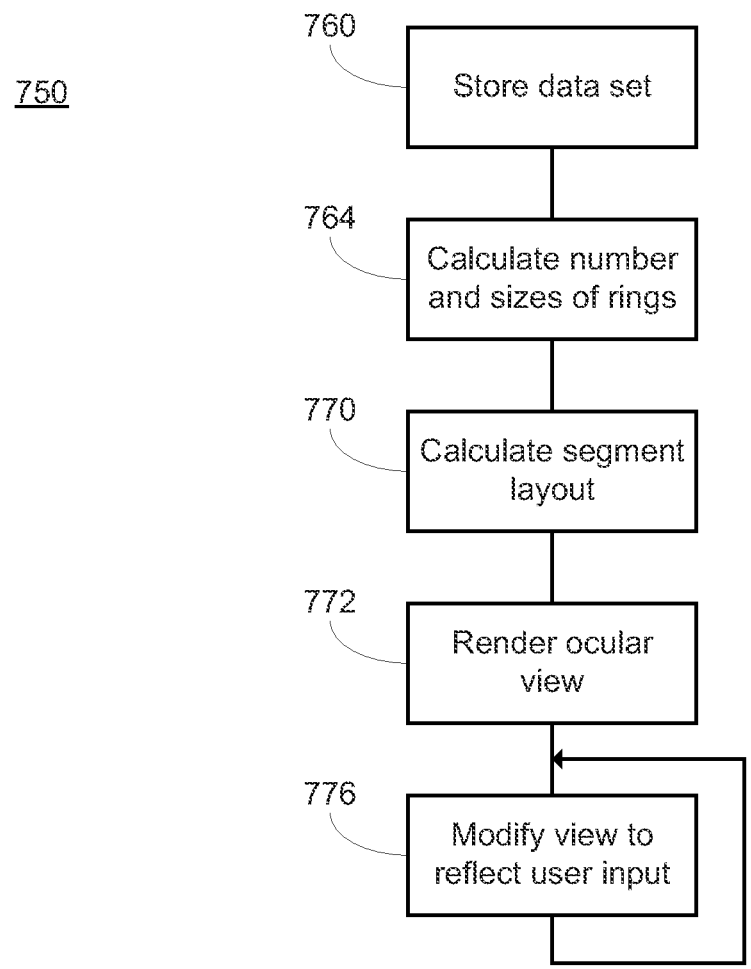
FIG. 11 depicts the flow of calculating the layout and rendering of an ocular view according to an embodiment of the invention.

Once the Web page has been generated by the server, the page may be transmitted to the browser in block 722. Any or all necessary layout information, if not computed by the server and explicitly or implicitly included in the page, may be computed by the browser as it renders the page. FIG. 11 depicts the flow 750 of such calculation and rendering according to an embodiment of the invention. The flow 750 begins with storing the data set, and/or information about its size and dimensionality sufficient to calculate the layout, in working storage (e.g., RAM).

In block 764, the number and sizes of the rings are calculated. In an embodiment of the invention, the number of rings may be equal to the number to the number of dimensions of the data set. Alternatively, in an embodiment of the invention, the rings may be demarcated by concentric circles; in such an embodiment, the number of circles will be one more than the number of dimensions.

The widths of some or all of the rings (and/or the diameters of the corresponding circles) may in an embodiment of the invention be such that a typical user would perceive it as an annular area and not just as a circle. Such a width may also be intended to provide a large enough area to make selection of a segment convenient, without requiring excessively fine control of a pointing device by a user. The width may be fixed numerically and set e.g., as a configured parameter and/or hard-coded into an implementation. Alternatively, some or all of the widths and/or diameters may be calculated dynamically based on one or more properties of the expected display. For example, if the segments of a ring are themselves expected to contain text, the width of the ring may depend in whole or in part upon the expected size of the text.

In an embodiment of the invention, calculation of the layout may involve calculating the sizes of circles needed to demarcate the rings and dividing the segments based on the number of data points. In an embodiment of the invention, the segments of the outermost ring are equal in size (or roughly so), and the segments of the inner rings depend on the respective numbers of associated segments in the immediately outer ring. In such an embodiment, the number of degrees that each segment in the outermost ring subtends may be obtained by dividing 360 by the number of data points in the highest dimension.

In an alternative embodiment of the invention, the segments in the outermost ring need not all be equal in size. For example, as FIG. 5 depicts, the segment 766 associated with serum HIV is wider than other segments in the ring 520, which may reflect, e.g., a minimum size for the associated segment 768 in the inner ring 525. That minimum size may in turn reflect, e.g., the space needed by the label "Other" in the segment 768.

The angular sizes of the segments in each ring other than the outermost may, in an embodiment of the invention, be equal to the sizes of the associated rings in each associated segment in the immediately outer ring. For example, with reference to FIG. 5, all segments 530 of the outermost ring 520 are the same size and subtend angles of equal sizes (allowing for minor variations inherent in projecting circular shapes onto a rectangular grid, e.g., as is commonly found in a computer display). The segment 550 of the inner ring 525 that corresponds to the pancreas is associated with three segments 540, 544, 548 of the outer ring 520 and therefore subtends an angle equal to the sum of the angles subtended by the three associated segments.

Returning to FIG. 11, once the number and sizes of the rings and segments have been calculated in block 764, the layout may be calculated in block 770. In an embodiment of the invention, the calculations may include, e.g., calculating X and Y coordinates for the centers of the rings and/or the circles that border them, as well as the relative or absolute angular positions of the edges of the segments.

In block 772, the results of these calculations may be used to render the Web page. for example, in an embodiment of the invention, some or all of the results may be used as parameters to, e.g., functions in one or more JavaScript libraries adapted to draw graphics and/or define regions in the page as the browser displays it, and/or to associate behavior with such regions. Suitable libraries include, e.g., publicly available libraries adapted to support vector graphics, and may include Raphael or SVG-VML-3D, among others.

In embodiments of the invention, the calculations and/or layout described above are dynamic; that is, the calculations are performed in response to a specific request for display of a data set as part of the process of providing the requested data set for display. This use of "dynamic" herein is meant in contrast to static displays, which may, e.g., associate one or more templates, which may be associated with one or more data sets and/or classes of data sets and include the layout information needed to provide an ocular view of such a set or sets.

Some or all calculations associated with dynamic display of a multi-dimensional data set according to an embodiment of the invention may be performed by a server, and some or all of them may be performed by a client, e.g., by a browser executing JavaScript included in a page or associated with it. Calculations performed by a server may be reflected in JavaScript statements, which may include e.g., assignments and/or function calls, that are included in the Web page. Calculations performed by the client may use values, which may include, e.g., values from the data set and/or the results of server-side calculations, and execute other code (e.g., from one or more JavaScript libraries) to make the needed calculations. The allocation of calculations between the client and the server in a particular embodiment of the invention may not necessarily affect whether the display may be considered "dynamic".

Finally, in block 776 of FIG. 11, the system may repeatedly detect user interaction, e.g., in the form of pointer movements and/or keystrokes, and update the view in response.

Figure 12:
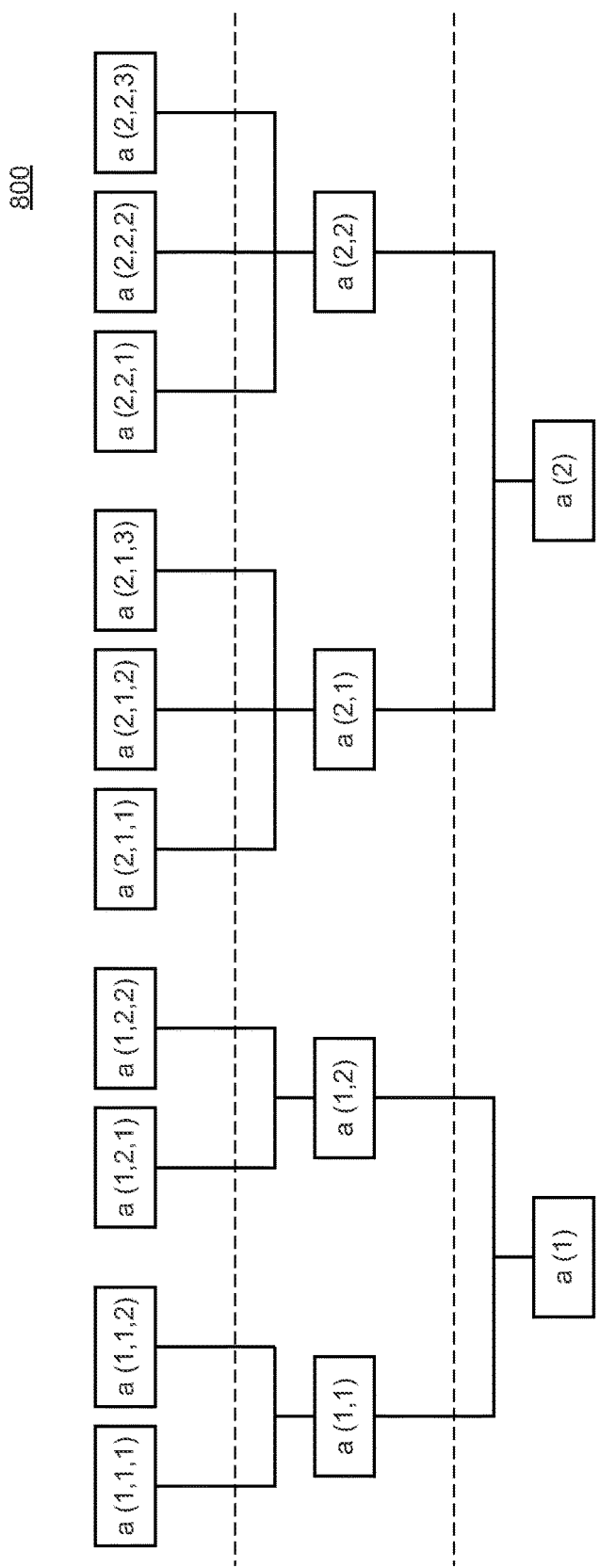
FIG. 12 depicts a three-dimensional data set such as may be displayed in connection with an embodiment of the invention.
Figure 13:
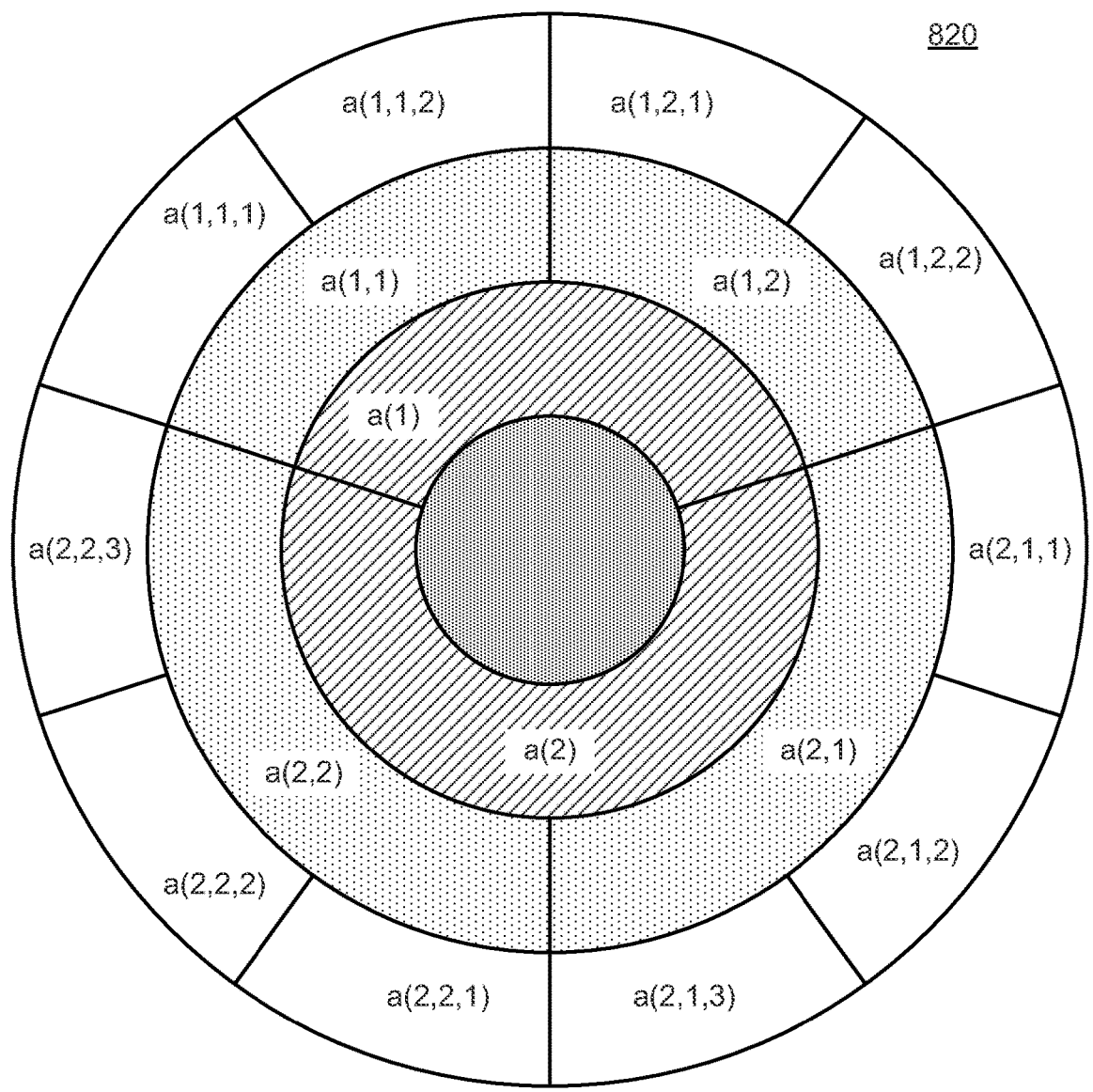
FIG. 13 depicts an ocular view of the data set of FIG. 12 according to an embodiment of the invention.

The invention has been illustrated in connection with two-dimensional data sets, but the invention is not limited to such sets. FIG. 12 depicts logically a three-dimensional data set 800, and FIG. 13 depicts an ocular view 820 of that data set. The application of the above principles to generation of the ocular view 820 of FIG. 13 from the data set 800 of FIG. 12 will be apparent to those skilled in the relevant arts.

The invention herein has been described in terms of certain embodiments. The reference to particular embodiments is meant to be illustrative and not limiting, and the invention is limited only by the claims herein.

The invention claimed is:

1. A computerized method for visually presenting a hierarchical data set, the method being performed by a computer system that comprises one or more processors and one or more interfaces operatively coupled to at least one of the processors, the method comprising:

receiving through at least one of the interfaces data that represents the hierarchical data set, the hierarchical data set comprising a plurality of data points in a plurality of hierarchical levels, the hierarchical levels being ordered from highest level to lowest level, and each data point comprising at least one value,
  wherein each data point in the second-lowest level of hierarchy of the data set represents an organ or body system, and each data point in the lowest level of hierarchy of the data set represents exactly one test result of the corresponding organ or body system;
responsive to receipt of the data, executing instructions on at least one of the processors to dynamically calculate layout data for an ocular view of the data set, the ocular view comprising a plurality of concentric annular regions surrounding a circular region and the layout data being dynamically calculated based on the received hierarchical data set so that
  (i) the annular regions are in one-to-one correspondence with the levels of hierarchy of the data set,
  (ii) each annular region is divided into contiguous segments, the number of segments in each respective annular region being equal to the number of data points in the corresponding level of hierarchy of the data set, and the segments in each respective annular region being in one-to-one correspondence with the data points in the corresponding level of hierarchy of the data set, and
  (iii) each segment displays at least one of the values in the respective corresponding data point;
transmitting through at least one of the interfaces information to cause an electronic display device to present the dynamically calculated ocular view of the data set;
after transmitting the information to cause an electronic display device to present the dynamically calculated ocular view of the data set, at least one of the processors executing instructions to determine that a user interface pointer is pointing at one of the segments in the annular region that corresponds to the lowest level of hierarchy; and
in response to the determination, transmitting through at least one of the interfaces information to cause the electronic display device to present in the circular region at least one of the values comprised by the data point corresponding to the segment being pointed to, without altering the one-to-one correspondence between the annular regions and the levels of hierarchy of the data set and without altering any of the one-to-one correspondences between the segments of the annular regions and the data points in the respective corresponding levels of hierarchy of the data set.

2. The method of claim 1, wherein:
each data point in each level of hierarchy other than the highest is associated respectively with exactly one of the data points in the immediately higher level of hierarchy; and
each data point in each level of hierarchy other than the lowest is associated respectively with one or more of the data points in the immediately lower level of hierarchy.

3. The method of claim 1, wherein:
(i) each segment of each annular region subtends respectively an angle that has its vertex at the center of the annular region, and
(ii) all the segments are mutually aligned so that the first angle subtended by a first segment overlaps with the second angle subtended by a second segment that is in an annular region immediately adjacent to the annular region containing the first segment if and only if the data point corresponding to the first segment is associated with the data point corresponding to the second segment.

4. The method of claim 1, comprising modifying the appearance of each segment to reflect at least one of the values in the corresponding data point.

5. The method of claim 4, wherein the color of each segment is modified according to at least one of the values in the respective corresponding data point.

6. The method of claim 1, comprising:
in response to the determination, transmitting through at least one of the interfaces information to cause the electronic display device to modify the appearance of the segment being pointed to.

7. The method of claim 1, comprising:
transmitting through at least one of the interfaces information to cause the electronic display device to present a separate information region contemporaneously with the ocular view; and
in response to the determination, transmitting through at least one of the interfaces information to cause the display to present in the separate information region information that is associated with at least one of the values comprised by a data point that is associated with the data point corresponding to the segment being pointed to.

8. A computer system for visually presenting a hierarchical data set, the computer system comprising:
one or more processors;
one or more interfaces operatively coupled to at least one of the processors; and
one or more computer-readable storage media operatively coupled to at least one of the processors and encoded with instructions that, when executed by at least one of the processors, cause the computer system at least to:
receive through at least one of the interfaces data that represents the hierarchical data set, the hierarchical data set comprising a plurality of data points in a plurality of hierarchical levels, the hierarchical levels being ordered from highest level to lowest level, and each data point comprising at least one value, wherein each data point in the second-lowest level of hierarchy of the data set represents an organ or body system, and each data point in the lowest level of hierarchy of the data set represents exactly one test result of the corresponding organ or body system,
responsive to receipt of the data, dynamically calculate layout data for an ocular view of the data set, the ocular view comprising a plurality of concentric annular regions surrounding a circular region and the layout data being dynamically calculated based on the received hierarchical data set so that (i) the annular regions are in one-to-one correspondence with the levels of hierarchy of the data set, (ii) each annular region is divided into contiguous segments, the number of segments in each respective annular region being equal to the number of data points in the corresponding level of hierarchy of the data set, and the segments in each respective annular region being in one-to-one correspondence with the data points in the corresponding level of hierarchy of the data set, and (iii) each segment displays at least one of the values in the respective corresponding data point,
transmit through at least one of the interfaces information to cause an electronic display device to present the dynamically calculated ocular view of the data set,
after transmitting the information to cause an electronic display device to present the dynamically calculated ocular view of the data set, determine that a user interface pointer is pointing at one of the segments in the annular region that corresponds to the lowest level of hierarchy, and
in response to the determination, transmitting through at least one of the interfaces information to cause the electronic display device to present in the circular region at least one of the values comprised by the data point corresponding to the segment being pointed to, without altering the one-to-one correspondence between the annular regions and the levels of hierarchy of the data set and without altering any of the one-to-one correspondences between the segments of the annular regions and the data points in the respective corresponding hierarchical levels of the data set.

9. The computer system of claim 8, wherein:
each data point in each level of hierarchy other than the highest is associated respectively with exactly one of the data points in the immediately higher level of hierarchy; and
each data point in each level of hierarchy other than lowest is associated respectively with one or more of the data points in the immediately lower level of hierarchy.

10. The computer system of claim 8, wherein:
(i) each segment of each annular region subtends respectively an angle that has its vertex at the center of the annular region; and
(ii) all the segments are mutually aligned so that the first angle subtended by a first segment overlaps with the second angle subtended by a second segment that is in an annular region immediately adjacent to the annular region containing the first segment if and only if the data point corresponding to the first segment is associated with the data point corresponding to the second segment.

11. The computer system of claim 8, wherein the instructions comprise instructions that cause the computer system at least to modify the appearance of each segment to reflect at least one of the values in the corresponding data point.

12. The computer system of claim 11, wherein the color of each segment is modified according to at least one of the values in the respective corresponding data point.

13. The computer system of claim 8, wherein the instructions comprise instructions that cause the computer system at least to:
in response to the determination, transmit through at least one of the interfaces information to cause the electronic display device to modify the appearance of the segment being pointed to.

14. The computer system of claim 8, wherein the instructions comprise instructions that cause the computer system at least to:
transmit through at least one of the interfaces information to cause the electronic display device to present a separate information region contemporaneously with the ocular view; and
in response to the determination, transmit through at least one of the interfaces information to cause the display to present in the separate information region information that is associated with at least one of the values comprised by a data point that is associated with the data point corresponding to the segment being pointed to.

15. A computer-readable storage medium encoded with instructions that, when executed by one or more processors within a computer system that comprises one or more interfaces operatively coupled to at least one of the processors, causes the computer system at least to:
receive through at least one of the interfaces data that represents a hierarchical data set, the hierarchical data set comprising a plurality of data points in a plurality of hierarchical levels, the hierarchical levels being ordered from highest level to lowest level, and each data point comprising at least one value,
wherein each data point in the second-lowest level of hierarchy of the data set represents an organ or body system, and each data point in the lowest level of hierarchy of the data set represents exactly one test result of the corresponding organ or body system;
responsive to receipt of the data, dynamically calculate layout data for an ocular view of the data set, the ocular view comprising a plurality of concentric annular regions surrounding a circular region and the layout data being dynamically calculated based on the received hierarchical data set so that
(i) the annular regions are in one-to-one correspondence with the levels of hierarchy of the data set,
(ii) each annular region is divided into contiguous segments, the number of segments in each respective annular region being equal to the number of data points in the corresponding level of hierarchy of the data set, and the segments in each respective annular region being in one-to-one correspondence with the data points in the corresponding level of hierarchy of the data set, and
(iii) each segment displays at least one of the values in the respective corresponding data point;
transmit through at least one of the interfaces information to cause an electronic display device to present the dynamically calculated ocular view of the data set;
after transmitting the information to cause an electronic display device to present the dynamically calculated ocular view of the data set, determine that a user interface pointer is pointing at one of the segments in the annular region that corresponds to the lowest level of hierarchy; and
in response to the determination, transmitting through at least one of the interfaces information to cause the electronic display device to present in the circular region at least one of the values comprised by the data point corresponding to the segment being pointed to, without altering the one-to-one correspondence between the annular regions and the levels of hierarchy of the data set and without altering any of the one-to-one correspondences between the segments of the annular regions and the data points in the respective corresponding levels of hierarchy of the data set.

16. The computer-readable storage medium of claim 15, wherein:
each data point in each level of hierarchy other than the highest is associated respectively with exactly one of the data points in the immediately higher level of hierarchy; and
each data point in each level of hierarchy other than the lowest is associated respectively with one or more of the data points in the immediately lower level of hierarchy.

17. The computer-readable storage medium of claim 15, wherein:
(i) each segment of each annular region subtends respectively an angle that has its vertex at the center of the annular region, and
(ii) all the segments are mutually aligned so that the first angle subtended by a first segment overlaps with the second angle subtended by a second segment that is in an annular region immediately adjacent to the annular region containing the first segment if and only if the data point corresponding to the first segment is associated with the data point corresponding to the second segment.

18. The computer-readable storage medium of claim 15, wherein the instructions comprise instructions that cause the computer system at least to modify the appearance of each segment to reflect at least one of the values in the corresponding data point.

19. The computer-readable storage medium of claim 18, wherein the color of each segment is modified according to at least one of the values in the respective corresponding data point.

20. The computer-readable storage medium of claim 15, wherein the instructions comprise instructions that cause the computer system at least to:
in response to the determination, transmit through at least one of the interfaces information to cause the electronic display device to modify the appearance of the segment being pointed to.

21. The computer-readable storage medium of claim 15, wherein the instructions comprise instructions that cause the computer system at least to:
transmit through at least one of the interfaces information to cause the electronic display device to present a separate information region contemporaneously with the ocular view; and
in response to the determination, transmit through at least one of the interfaces information to cause the display to present in the separate information region information that is associated with at least one of the values comprised by a data point that is associated with the data point corresponding to the segment being pointed to.

* * * * *